United States Patent
Ma Schwab

[11] Patent Number: 5,827,225
[45] Date of Patent: Oct. 27, 1998

[54] CATHETER FLEXIBLE DISTAL TIP

[75] Inventor: Sharon Ma Schwab, Encinitas, Calif.

[73] Assignee: Medtronic, Inc., Minneapolis, Minn.

[21] Appl. No.: 787,076

[22] Filed: Jan. 22, 1997

Related U.S. Application Data

[63] Continuation of Ser. No. 312,359, Sep. 26, 1994, abandoned.

[51] Int. Cl.⁶ .................................................. A61M 25/00
[52] U.S. Cl. ............................................. 604/96; 606/194
[58] Field of Search ..................... 604/96, 103; 606/192, 606/194; 128/656–658

[56] References Cited

U.S. PATENT DOCUMENTS

| | | | |
|---|---|---|---|
| 4,739,768 | 4/1988 | Engelson | 128/658 |
| 4,877,031 | 10/1989 | Conway et al. | 604/96 X |
| 4,892,519 | 1/1990 | Songer et al. | 604/96 |
| 5,344,402 | 9/1994 | Crocker | 604/96 |
| 5,370,615 | 12/1994 | Johnson | 604/96 |
| 5,437,632 | 8/1995 | Engelson | 604/53 |

FOREIGN PATENT DOCUMENTS

| | | | |
|---|---|---|---|
| 0184314 | 6/1986 | European Pat. Off. | A61M 29/02 |
| 0597465 | 9/1987 | European Pat. Off. | A61M 29/02 |

*Primary Examiner*—Corrine M. McDermott
*Attorney, Agent, or Firm*—Dianne M. F. Plunkett; Harold R. Patton

[57] ABSTRACT

The catheter (5) with a flexible tip (20) includes a manifold (25) at the proximal end, a flexible catheter body (40) having a proximal end and a distal end, a balloon (15) at the distal end and a distal flexible tip (20). The catheter is designed for operation as an "over the wire" catheter and would be compatible with a flexible guidewire, such as guidewire (30). The flexible tip invention also would be compatible with "rapid exchange" or "single operator exchange" catheters. Flexible tip (20) extends distally from balloon (15) and guidewire shaft (55). In the preferred embodiment flexible tip (20) is formed from distal material of balloon (15). The length of the flexible tip (20) will vary depending on the path that catheter (5) must travel through the artery to get to its desired location. The length of the tip will balance the pushability desired versus the flexibility desired. A longer flexible tip (20) on catheter (5) would allow enough flexibility at the tip for catheter (5) to get at hard to reach lesions through a tortuous path. A shorter flexible tip (20) on catheter (5) would make the tip stiffer and allow higher pushability through blocked arteries. By varying the flexible tip (20), the catheter 5 may be designed for many different conditions.

5 Claims, 1 Drawing Sheet

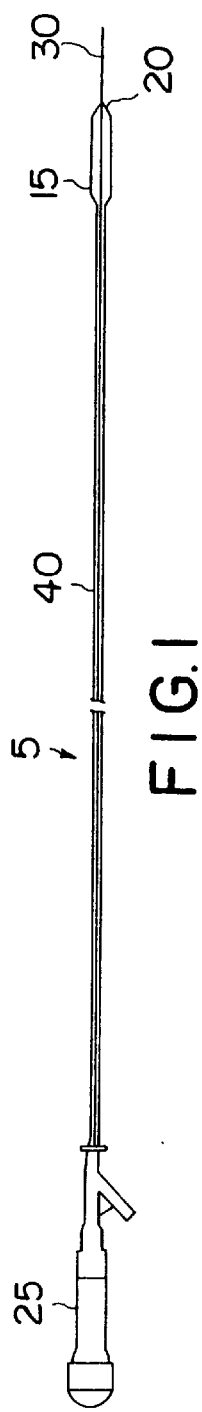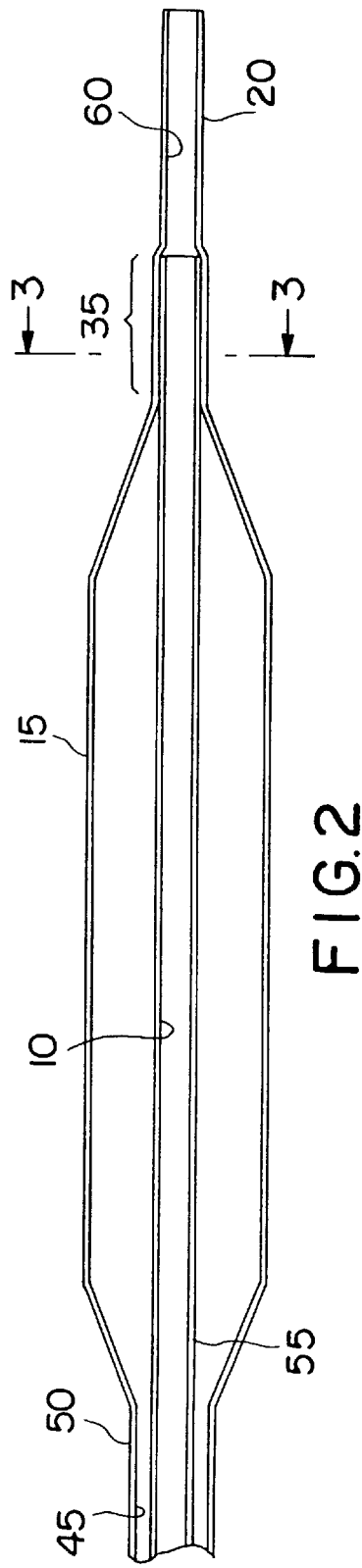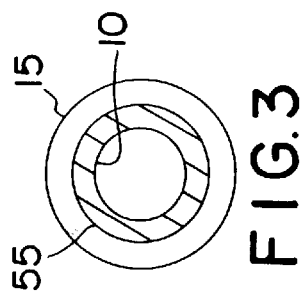

CATHETER FLEXIBLE DISTAL TIP

This application is a continuation of application Ser. No. 08/312,359 filed on Sep. 26, 1994, now abandoned.

FIELD OF THE INVENTION

The present invention relates to the field of angioplasty, and more particularly, to a flexible tip of a dilatation balloon catheter.

BACKGROUND OF THE INVENTION

Dilatation balloon catheters are frequently used for the treatment of stenosis in the coronary arteries. This procedure, known as percutaneous transluminal coronary angioplasty (PCTA), was developed by Dr. Andreas Gruntzig. According to this procedure, blockage in a coronary artery can be reduced by positioning a balloon dilatation catheter across the blockage and inflating the balloon, which causes stretching of the artery and pressing of the lesion into the artery wall to re-establish acceptable blood flow through the artery. The first marketable PCTA catheters for angioplasty were "fixed wire" catheters, in which a core or guidewire was fixed within the catheter to stiffen it so that it could be pushed into position in the vascular system.

Dr. John Simpson and Dr. Edward Robert subsequently developed an "over-the-wire" catheter in which a guidewire was slidably placed within a lumen of the catheter. The guidewire lumen passed from the distal end of the catheter through the balloon to the proximal end of the catheter. This system provided reasonably easy placement of the catheter because the guidewire was inherently smaller and more flexible than the fixed wire system so one could more readily select the desired coronary artery and reach smaller branches. Once the guidewire was positioned beyond the stenosis, the catheter was then slid over the guidewire so that placement of the balloon spanned the stenosis and the balloon was then inflated.

The design of medical devices for insertion into body organs has always involved trading off various performance characteristics in the design of a satisfactory implement. To allow ease of movement through the artery, the dilatation balloon diameter should be as small as possible. To minimize the diameter of the catheter, the balloon is folded, wrapped or twisted to achieve the smallest profile. This deflated diameter affects the ease and ability of the dilatation catheter to pass through a guide catheter and through the coronary arteries leading to the stenosis to be opened. Some applications require a device which is stiff enough to be pushable and go through blockage, while being flexible enough to go around bends. The flexibility of the tip section of such devices have been of particular interest for insertion of guidewires and catheters into arteries that require the device follow a tortuous path through small arteries. For this, great flexibility is required.

U.S. Pat. No. 4,739,768 to Erik T. Engelson for "CATHETER FOR GUIDE-WIRE TRACKING" discloses a drug delivery catheter with a relatively stiff proximal segment and a relatively flexible distal segment that is at least 5 cm long and can be advanced along a guidewire placed in a tortuous vascular path and provides a method for delivery of a injectable fluid at a tissue site. While the distal segment itself may be very flexible and works well for drug delivery, it is too long and flexible to achieve pushability sufficient enough to push through a blockage in the artery or stenosis.

Today's common dilatation balloons catheters have the lumen pass through the balloon and the balloon and lumen are bonded at the distal end. This makes the tip of the dilatation catheter a relatively rigid structure and a rigid tip is desired for pushing the dilatation balloon catheter through a stenosis or blocked artery. If the tip of the catheter is too stiff, it may not be able to navigate sharp turns to get to the stenosis. This limits the effectiveness of the dilatation balloon catheter to only easy to reach arteries of the heart. A dilatation catheter with a flexible tip would be useful in the treatment of lesions that have been traditionally inaccessible to balloon catheters. It can be seen that these characteristics, while easily accomplished in a large device, may be mutually exclusive in a very small diameter device such as a catheter for coronary arteries. What is needed is a structure which provides the needed pushability and force transmission in the tip area to push through blockage in the artery while being flexible to navigate tortuous path and sharp curves through small arteries.

SUMMARY OF THE INVENTION

Accordingly, the present invention is directed to an improved distal tip (flex tip) of a dilatation balloon catheter. The flexible tip extends beyond the distal end of the guidewire lumen to allow the dilatation balloon catheter to navigate sharp curves and still have the pushability at the tip to go through blocked arteries. The characteristics of the flexible tip can be varied by altering the length of the tip. The longer flexible tip allows more flexibility and less pushability while the shorter flexible tip has higher pushability. The dilatation balloon catheter with the flexible tip comprises a catheter body with an inflatable balloon in fluid communication with an inflation lumen mounted on the distal end of the catheter body and a guidewire lumen extending through the balloon. The flexible tip is formed from balloon material distally extending beyond the guidewire lumen with a inner diameter generally equal to the inner diameter of the guidewire lumen. In the preferred embodiment the balloon and flexible tip is made of low density polyethylene (LDPE) while the catheter body is made of high density polyethylene (HDPE).

BRIEF DESCRIPTION OF THE DRAWINGS

The foregoing and other features of the present invention will be best appreciated with reference to the following detailed description of a specific embodiment of the invention, when read in conjunction with the accompanying drawings.

FIG. 1 is a side plan view of a catheter constructed according to the present invention partially broken away.

FIG. 2 is a cross-sectional view of a distal portion of the catheter in FIG. 1.

FIG. 3 is an enlarged cross-sectional view taken along line 3—3 in FIG. 2.

DETAILED DESCRIPTION OF THE PREFERRED EMBODIMENTS

FIG. 1 shows an over the wire catheter 5 with the present invention, which includes a manifold 25 at the proximal end, a flexible catheter body 40 having a proximal end and a distal end, a balloon 15 at the distal end and a flexible tip 20. The catheter is designed for operation as an "over the wire" catheter and would be compatible with a flexible guidewire, such as guidewire 30. The flexible tip invention also would be compatible with "rapid exchange" or "single operator exchange" catheters.

FIG. 2 shows a cross-sectional view of the distal end of a over the wire dilatation balloon catheter 5 according to the present invention with guidewire 30 omitted for clarity. The catheter body 40 includes a shaft 50 having a proximal end and a distal end defining inflation lumen 45. Inflation lumen 45 is in fluid communication with the proximal end of balloon 15. Mounted within the inflation lumen 45 is a smaller diameter guidewire shaft 55 having a proximal end and a distal end defining guidewire lumen 10. Guidewire lumen 10 has a diameter larger than guidewire 30 to allow sliding of the catheter 5 over guidewire 30. The distal end of balloon 15 is sealingly mounted on the distal end of guidewire shaft 55 as shown at 35. In the preferred embodiment the bond at 35 is formed by heat shrinking the balloon 15 to the guidewire shaft 55. FIG. 3 shows balloon 15 sealingly mounted on guidewire shaft 55 and also guidewire lumen 10. In the preferred embodiment, the catheter body 40 is made of high density polyethylene (HDPE) while the balloon 15 and flexible tip 20 is made of low density polyethylene (LDPE). Flexible tip 20 includes proximal and distal ends and a inner lumen 60. Flexible tip 20 extends distally from balloon 15 and guidewire shaft 55. In the preferred embodiment flexible tip 20 has a length up to 5 cm and is formed from distal material of balloon 15. The inner lumen 60 should have a diameter generally equal to guidewire lumen 10 so that guidewire 30 will not snag.

The method of using the invention is as follows:

At the beginning of a PTCA procedure, guidewire 30 is inserted into the body. The guidewire 30 itself must be flexible and small enough to go through the artery and to navigate tortuous paths to reach the lesion. After guidewire 30 is in the correct position, the over the wire catheter 5 can be now be advanced over guidewire 30. The flexible tip 20 allows catheter 5 to track over guidewire 30 through tight curves and push through blocked arteries until balloon 15 is positioned over the lesion. Once balloon 15 is in place over the lesion, it can now be used for dilatation.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|---|---|
| 5 | Catheter |
| 10 | Guidewire Lumen |
| 15 | Balloon |
| 20 | Flexible tip |
| 25 | Manifold |
| 30 | Guidewire |
| 35 | Bond |
| 40 | Catheter Body |
| 45 | Inflation Lumen |
| 50 | Shaft |
| 55 | Guidewire Shaft |
| 60 | Inner Lumen |

What is claimed is:

1. A dilatation balloon catheter with a flexible tip comprising:

(a) a catheter body having proximal and distal ends with an outer shaft defining an inflation lumen and an inner guidewire shaft defining a guidewire lumen, the guidewire shaft having a proximal end, a distal end, an inner diameter and an outer diameter, the inner guidewire shaft extending longitudinally through the outer shaft inflation lumen;

(b) an inflatable balloon mounted at the distal end of the catheter body, the balloon having a distal end and a proximal end, the proximal end of the balloon in fluid communication with the distal end of the inflation lumen and the distal end of the balloon sealingly mounted to the distal end of the inner guidewire shaft to form a distal bond, the distal bond having a proximal end and a distal end; and (c) a flexible tip defining an inner lumen, the flexible tip having an inner diameter and an outer diameter, the flexible tip being formed from the distal end of the balloon material distally extending beyond the distal end of the guidewire shaft, the inner diameter of the flexible tip being equal to the inner diameter of the guidewire shaft from the proximal end of the balloon to the distal end of the flexible tip, the flexible tip having a proximal end and a distal end, the proximal end of the tip abutting the distal end of the guidewire shaft.

2. The dilatation balloon catheter of claim 1 wherein the balloon and flexible tip is made of low density polyethylene (LDPE).

3. The dilatation balloon catheter of claim 1 wherein the catheter body is made of high density polyethylene (HDPE).

4. The dilatation balloon catheter of claim 1 wherein the flexible tip has a length up to 5 cm.

5. A dilatation balloon catheter with a flexible tip comprising:

(a) a catheter body having proximal and distal ends with an outer shaft defining an inflation lumen and an inner guidewire shaft defining a guidewire lumen, the guidewire shaft having a proximal end, a distal end, an inner diameter and an outer diameter, the inner guidewire shaft extending longitudinally through the outer shaft inflation lumen:

(b) an inflatable balloon mounted at the distal end of the catheter body, the balloon having a distal end and a proximal end, the proximal end of the balloon in fluid communication with the distal end of the inflation lumen and the distal end of the balloon sealingly mounted to the distal end of the inner guidewire shaft to form a distal bond the distal bond having a proximal end and a distal end; and (c) a flexible tip defining an inner lumen, the flexible tip having an inner diameter and an outer diameter the flexible top being formed from the distal end of the balloon material distally extending beyond the distal end of the guidewire shaft, the inner diameter of the flexible tip being equal to the inner diameter of the guidewire shaft from the proximal end of the balloon to the distal end of the flexible tip, the flexible tip having a proximal end and a distal end, the proximal end of the tip abutting the distal end of the guidewire shaft, the tip with a length up to 5 cm.

* * * * *